United States Patent

Yamamoto et al.

[11] Patent Number: 5,563,070
[45] Date of Patent: Oct. 8, 1996

[54] METHOD OF COUNTING RETICULOCYTES

[75] Inventors: Kohji Yamamoto, Kyoto; Muneo Tokita, Nagaokakyo; Misako Inagami, Takatsuki; Sinichi Hirako, Nagaokakyo, all of Japan

[73] Assignee: OMRON Corporation, Japan

[21] Appl. No.: 249,576

[22] Filed: May 26, 1994

[30] Foreign Application Priority Data

May 28, 1993 [JP] Japan .................................... 5-126651

[51] Int. Cl.⁶ .................................................. G01N 33/48
[52] U.S. Cl. ............................ 436/63; 436/10; 436/164; 436/172; 436/800; 435/2; 435/6; 435/29; 435/34
[58] Field of Search .............................. 436/10, 63, 164, 436/172, 800; 435/2, 4, 6, 29, 34, 808; 422/82.05, 82.08; 536/23.1; 546/176, 165, 270, 271

[56] References Cited

U.S. PATENT DOCUMENTS

| | | | |
|---|---|---|---|
| 4,325,706 | 4/1982 | Gershman et al. | 436/63 |
| 4,336,029 | 6/1982 | Natale | 436/172 |
| 4,571,388 | 2/1986 | O'Connell et al. | 436/63 |
| 4,707,451 | 11/1987 | Sage, Jr. | 436/63 |
| 4,883,867 | 11/1989 | Lee et al. | 536/28 |
| 4,957,870 | 9/1990 | Lee et al. | 436/63 |
| 4,981,803 | 1/1991 | Kuroda | 436/63 |
| 5,075,556 | 12/1991 | Fan et al. | 436/63 X |
| 5,321,130 | 6/1994 | Yue et al. | 536/23.1 |
| 5,350,695 | 9/1994 | Colella et al. | 436/63 |
| 5,410,030 | 4/1995 | Yue et al. | 536/23.1 |
| 5,418,169 | 5/1995 | Crissman et al. | 436/94 |
| 5,436,134 | 7/1995 | Haugland et al. | 435/34 |
| 5,437,980 | 8/1995 | Haughland | 435/6 |

FOREIGN PATENT DOCUMENTS

| | | |
|---|---|---|
| 05040097 | 2/1993 | Japan . |
| 5287209 | 11/1993 | Japan . |
| 9306482 | 4/1993 | WIPO . |

OTHER PUBLICATIONS

Rye et al. Analytical Biochemistry, vol. 208, pp. 144–150, Jan. 1993.

H. S. Rye et al., Stable Fluorescent Complexes of Double-Stranded DNA with Bis–Intercalating Asymmetric Cyanine Dyes: Properties and Applications, Nucleic Acids Research, vol. 20, No. 11, 1992 Oxford U. Press.

*Primary Examiner*—Jill Warden
*Assistant Examiner*—Maureen M. Wallenhorst
*Attorney, Agent, or Firm*—Fish & Richardson, P.C.

[57] ABSTRACT

The invention provides a method of quantitating reticulocytes with high sensitivity and high accuracy at low cost employing a fluorescent dye suitable for the staining of reticulocytes. A blood sample stained with a fluorescent dye composition containing TOTO-3, TO-PRO-3, POPO-3, PO-PRO-3, YOYO-1, YO-PRO-1, YOYO-3 or YO-PRO-3 as the fluorescent dye is exposed to light in the red-wave length region in the case of TOTO-3 or TO-PRO-3, light in the green region for POPO-3 or PO-PRO-3, light in the blue region for YOYO-1 or YO-PRO-1, or light in the orange region for YOYO-3 or YO-PRO-3 and the resultant fluorescent emission from the blood sample is measured to enumerate reticulocytes.

16 Claims, 13 Drawing Sheets

| GRAPH NO. 1 | | | | | | | |
|---|---|---|---|---|---|---|---|
| Gate | Count | Total % | Mean X | Mean Y | CV%X | CV%Y |
| Tot | 58,592 | 100.0 | 58.4 | 48.2 | 36.0 | 136.1 |
| A | 10,210 | 17.4 | 65.8 | 182.4 | 27.1 | 9.1 |
| B | | | | | | |
| C | | | | | | |

| GRAPH NO. 2 | | | | |
|---|---|---|---|---|
| REG | Posi% | Count | Mean | SD | CV% |
| − | 94.3 | 9,631 | 63.4 | 13.0 | 20.5 |
| + | 5.7 | 579 | 115.2 | 14.4 | 12.5 |

GRAPH NO. 1

| Gate | Count | Total % | Mean X | Mean Y | CV%X | CV%Y |
|---|---|---|---|---|---|---|
| Tot | 10,691 | 100.0 | 26.8 | 182.6 | 112.7 | 16.4 |
| A | 10,001 | 93.5 | 22.4 | 190.0 | 100.0 | 4.1 |
| B | | | | | | |
| C | | | | | | |

GRAPH NO. 3

| REG | Posi% | Count | Mean | SD | CV% |
|---|---|---|---|---|---|
| − | 97.7 | 9,771 | 21.3 | 20.4 | 95.8 |
| + | 2.3 | 230 | 85.9 | 17.4 | 20.3 |

GRAPH NO. 1

| Gate | Count | Total % | Mean X | Mean Y | CV%X | CV%Y |
|---|---|---|---|---|---|---|
| Tot | 10,601 | 100.0 | 25.0 | 183.4 | 117.6 | 15.3 |
| A | 10,001 | 94.3 | 21.0 | 189.8 | 102.9 | 3.8 |
| B | | | | | | |
| C | | | | | | |

GRAPH NO. 3

| REG | Posi% | Count | Mean | SD | CV% |
|---|---|---|---|---|---|
| − | 98.1 | 9,816 | 20.0 | 19.9 | 99.5 |
| + | 1.9 | 186 | 86.8 | 17.3 | 19.9 |

GRAPH NO. 1

| Gate | Count | Total % | Mean X | Mean Y | CV%X | CV%Y |
|---|---|---|---|---|---|---|
| Tot | 10,070 | 100.0 | 8.8 | 100.2 | 159.1 | 5.9 |
| A | 10,001 | 99.3 | 8.4 | 190.8 | 152.4 | 4.4 |
| B | | | | | | |
| C | | | | | | |

GRAPH NO. 3

| REG | Posi% | Count | Mean | SD | CV% |
|---|---|---|---|---|---|
| − | 99.9 | 9,993 | 8.5 | 12.7 | 149.4 |
| + | 0.1 | 8 | 105.9 | 23.2 | 21.9 |

METHOD OF COUNTING RETICULOCYTES

FIELD OF THE INVENTION

This invention relates to a method of quantitating reticulocytes in blood. More particularly, the invention relates to a method and apparatus for quantitating reticulocytes with the aid of a dye suited for staining the ribonucleic acid (RNA) component of the reticulocytes.

BACKGROUND OF THE INVENTION

The immature erythrocytes in blood are called reticulocytes and the reticulocyte count is considered to be a laboratory parameter of great significance in the diagnosis of acute internal hemorrhage and hemolytic anemia, among other diseases. This is because reticulocytes serve as an indicator of blood cell production (erythrocyte differentiation).

It is also known that the reticulocyte has RNA and in the determination of reticulocytes, it is common practice to stain a blood smear with new methylene blue (NMB), brilliant cresyl blue (BCB) or the like and count the stained reticulocytes under the microscope. There also are alternative procedures, either manual or automatic, which employ fluorescent dyes such as acrydine orange, pyronine Y, thioflavin T, auramine O, thiazole orange and so on.

The ultravital staining technique using new methylene blue has been employed as the standard method for enumerating reticulocytes but being a manual procedure, this technique is time-consuming and complicated and has the drawback of individual difference according to different observers.

The determination technique employing acrydine orange is either manual or automatic as disclosed in, inter alia, U.S. Pat. Nos. 4,336,029, 4,325,706 and 4,284,412. Thus, acrydine orange couples itself to the RNA component of reticulocytes to produce a red fluorescence and the number of reticulocytes is determined by measuring the emissions. However, the RNA is precipitated by acrydine orange and localized within the cell so that the quantitation of fluorescence tends to lack accuracy. Moreover, this dye has a high affinity for the quartz cell and plastic materials constituting the circuitry of a flow cytometer.

Determination with pyronine Y requires a prior formalin fixation of red blood cells and is disadvantageous in that the technique is complicated and time-consuming. Furthermore, the fluorescent quantum efficiency of pyronine Y is so low that no sufficient sensitivity can be expected.

Thioflavin T is disclosed in Japanese Patent Application Kokai S-59-142465 as a reticulocyte stain but since it requires sufficient washing for reducing the noise of non-specific fluorescence, determination with this dye has the disadvantage that it requires a complicated and time-consuming procedure.

Auramine O and thiazole orange produce fluorescent emissions when excited by blue light but when a helium-cadmium laser is used as a light source in flow cytometry, the required equipment has to be large in size and expensive and the RNA specificity of these dyes is relatively lower than their specificity to DNA and protein.

Thus, the prior art determination techniques for enumerating reticulocytes using a flow cytometer have their own problems relating to sensitivity, accuracy and/or cost.

It is, therefore, a primary object of this invention to provide a means which enables sensitive, accurate and inexpensive determinations of reticulocytes using a dye suitable for staining reticulocytes.

SUMMARY OF THE INVENTION

This invention relates, in one aspect, to a method of quantitating reticulocytes which comprises exposing a blood sample stained with a fluorescent dye composition containing TOTO-3 or TO-PRO-3 as a fluorescent dye to light in the red wavelength region and measuring the fluorescence output from said blood sample.

This invention relates, in a second aspect, to a method of quantitating reticulocytes which comprises exposing a blood sample stained with a fluorescent dye composition containing POPO-3 or PO-PRO-3 as the fluorescent dye to light in the green wavelength region and measuring the output fluorescence from said blood sample.

This invention further relates, in a third aspect, to a method of quantitating reticulocytes which comprises exposing a blood sample stained with a fluorescent dye composition containing YOYO-1 or YO-PRO-1 as a fluorescent dye to light in the blue wavelength region and measuring the fluorescence output from said blood sample.

This invention relates, in a fourth aspect, to a method of quantitating reticulocytes which comprises exposing a blood sample stained with a fluorescent dye composition containing YOYO-3 or YO-PRO-3 as a fluorescent dye to light in the orange wavelength region and measuring the fluorescence output from said blood sample.

This invention further relates to a flow cytometric apparatus for practicing any of the above methods.

Figure 1A:
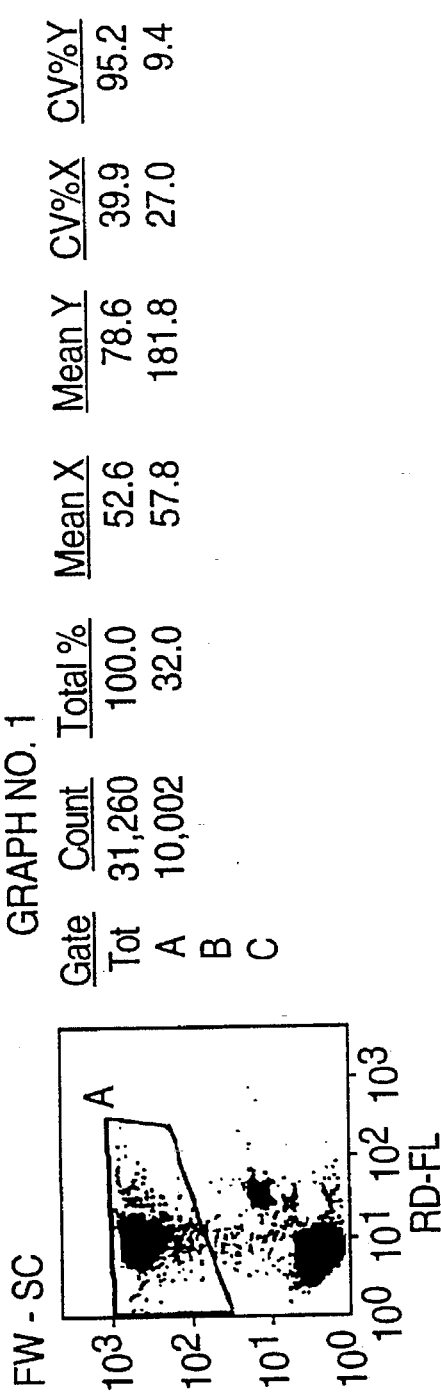
FIG. 1 shows the forward scatter versus red fluoresence cytogram and red fluorescence histogram of a normal blood sample stained with the fluorescent dye composition.

TOTO-3, the fluorescent dye which can be used in the first method, is a thiazole orange derivative homodimer of the following structure (chemical formula 1):

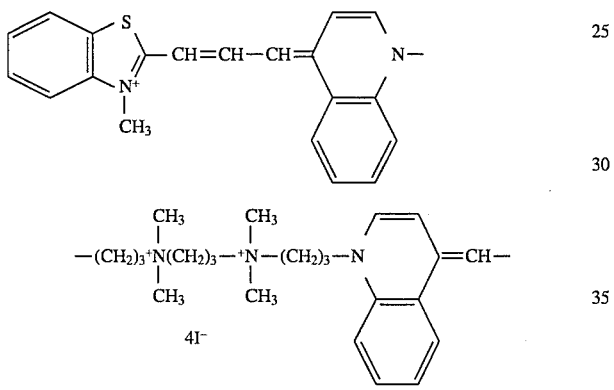

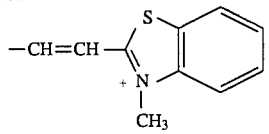

TO-PRO-3, which can also be used in the above method, is a quinolinium monomer of the following structure (chemical formula 2):

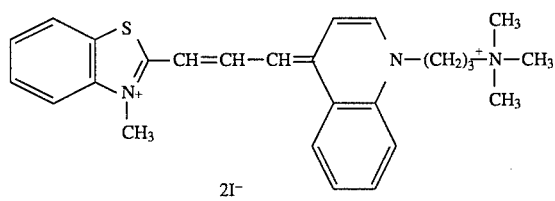

POPO-3, the fluorescent dye which can be used in the second method, is a dimerized benzoxazolium-4-pyridinium compound of the following structure (chemical formula 3):

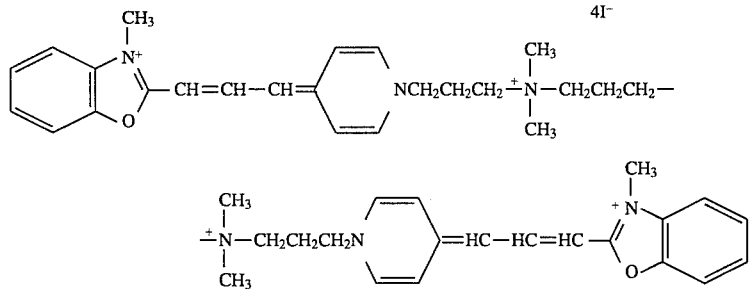

PO-PRO-3, which can also be used in the second method, is a benzoxazolium-4-pyridinium derivative of the following structure (chemical formula 4):

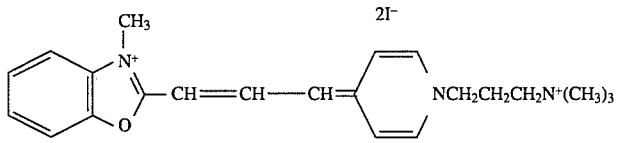

YOYO-1, the fluorescent dye which can be used in the third method, is a dimerized benzoxazolium-4-quinolinium compound of the following structure (chemical formula 5):

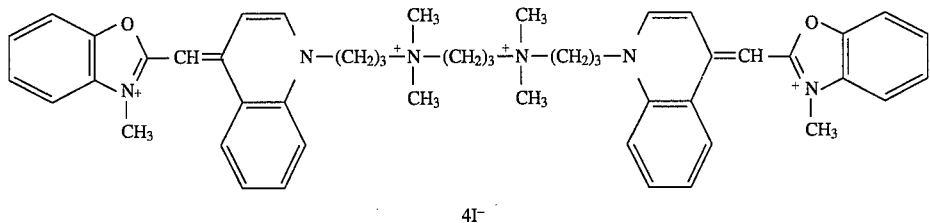

YO-PRO-1, which can also be used in the third method, is a benzoxazolium-4-quinolinium derivative of the following structure (chemical formula 6):

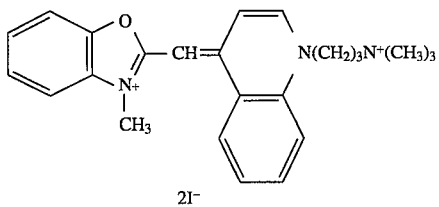

YOYO-3, the fluorescent dye which can be used in the fourth method, is a dimerized benzoxazolium-4-quinolinium compound of the following structure (chemical formula 7):

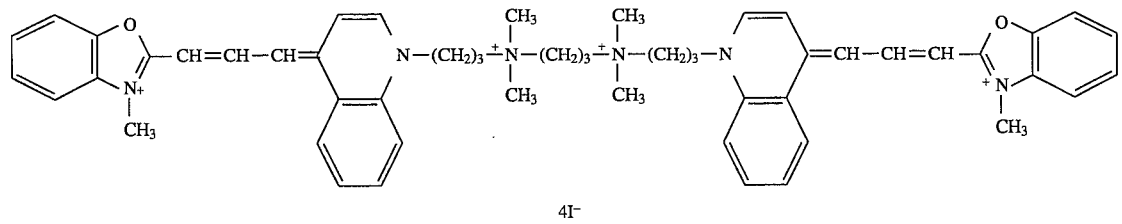

YO-PRO-3, the fluorescent dye which can also be used in the fourth method, is a benzoxazolium-4-quinolinium compound derivative of the following structure (chemical formula 8):

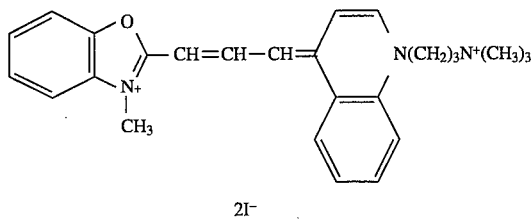

TOTO-3 and TO-PRO-3, POPO-3 and PO-PRO-3, YOYO-1 and YO-PRO-1, and YOYO-3 and YO-PRO-3, mentioned above, have all the advantage that whereas they produce little or no fluorescence when uncoupled to the RNA of reticulocytes, these compounds produce intense fluorescence when coupled to the RNA.

Therefore, in order to make the most of this advantage, the reticulocytes in blood are stained with a solution of TOTO-3 or TO-PRO-3, POPO-3 or PO-PRO-3, YOYO-1 or YO-PRO-1, or YOYO-3 or YO-PRO-3 in isotonic saline containing a small amount of dimethyl sulfoxide (DMSO) (each solution is hereinafter referred to as the fluorescent dye composition). The blood is stained on addition of such fluorescent dye composition and the stained blood gives a fluorescent emission on exposure to light depending on the wavelength of the exciting light, viz. the red wavelength when the dye is TOTO-3 or TO-PRO-3, the green wavelength in the case of POPO-3 or PO-PRO-3, the blue wavelength in the case of YOYO-1 or YO-PRO-1, or the orange wavelength in the case of YOYO-3 or YO-PRO-3, thus allowing reticulocytes in a blood sample to be detected and quantitated.

TOTO-3 or TO-PRO-3 has an excitation spectral peak at about 642 nm and a maximum peak of fluorescence at about 660 nm. Therefore, the light source for flow cytometry is preferably be a helium-neon laser (633 nm) which is inexpensive, although a mercury lamp having an emission line of 615 nm, a red super bright LED, a red laser diode, a mercury-xenon lamp or the like can likewise be employed.

POPO-3 or PO-PRO-3 has an excitation spectral peak of about 540 nm and a maximum peak of fluorescence at about 570 nm. Therefore, in the flow cytometric determination with the dye, it is advantageous, cost-wise as well as efficiency-wise, to employ a green helium-neon laser having an excitation spectral peak at about 540 nm ($\lambda p=543$ nm), a green super bright LED ($\lambda p=567$ nm) or a green laser diode.

YOYO-1 or YO-PRO-1 has an excitation spectral peak at about 490 nm and a maximum peak of fluorescence at about 510 nm. Therefore, the light source for a flow cytometer is preferably an argon ion laser having an excitation spectral peak at about 490 nm ($\lambda p=488$ nm), a blue super bright LED (Nichia Kagaku Kogyo, $\lambda p=450$ nm) or a blue laser diode.

YOYO-3 or YO-PRO-3 has an excitation spectral peak at about 612 nm and a maximum peak of fluorescence at about 630 nm. Therefore, as the light source for a flow cytometer, an orange helium-neon laser having an excitation spectral peak at about 612 nm ($\lambda p=594$ nm), an orange super bright LED and an orange laser diode are expedient, inexpensive and, therefore, advantageous.

Of course, as the light source for POPO-3 or PO-PRO-3, YOYO-1 or YO-PRO-1, or YOYO-3 or YO-PRO-3, a halogen lamp, a mercury-xenon lamp or the like can likewise be employed.

The fluorescent dye composition of this invention does not precipitate RNA and, therefore, the stained reticulocytes produce fluorescent emissions uniformly distributed within the cell. This means that an approximately first-order relation holds between the intensity of fluorescence of each reticulocyte and the RNA content of the same reticulocyte.

Clinically, the RNA content can be used as an indicator of differentiation of erythrocytes. Therefore, not only the reticulocyte count but also the fluorescence intensity data may provide new clinical information on the differentiation of red blood cells.

Thus, flow cytometry in accordance with this invention offers the advantage that both the reticulocyte count and the fluorescence intensity distribution can be determined at high speed, expediently and objectively. Of course, the method of this invention not only enables an automatic quantitation of reticulocytes but may be practiced on a manual mode.

In the field determination of reticulocytes by flow cytometry, the threshold value of red, green, blue or orange fluorescence is previously established using an unstained control (blank) sample, an enumeration is then performed using a stained sample and the reticulocytes satisfying the threshold value are counted.

Many flow cytometers are well known in the art and this invention is not limited to the use of any specific flow cytomer model.

EXAMPLES

The following examples are intended to illustrate some typical procedures for quantitation of reticulocytes according to this invention.

EXAMPLE 1

A 1 mM stock fluorescent dye solution (TOTO-3 or TO-PRO-3/DMSO) is prepared. This stock solution is diluted 1:20 with isotonic phosphate buffer at pH 7.4 and 5 µl of whole blood is added to 1 ml of the diluted fluorescent dye composition. The mixture is incubated at room temperature for about 30 minutes to prepare a blood sample and using a helium-neon laser having an excitation wavelength of 633 nm, the blood sample is subjected to flow cytometric determination.

Figure 1B:
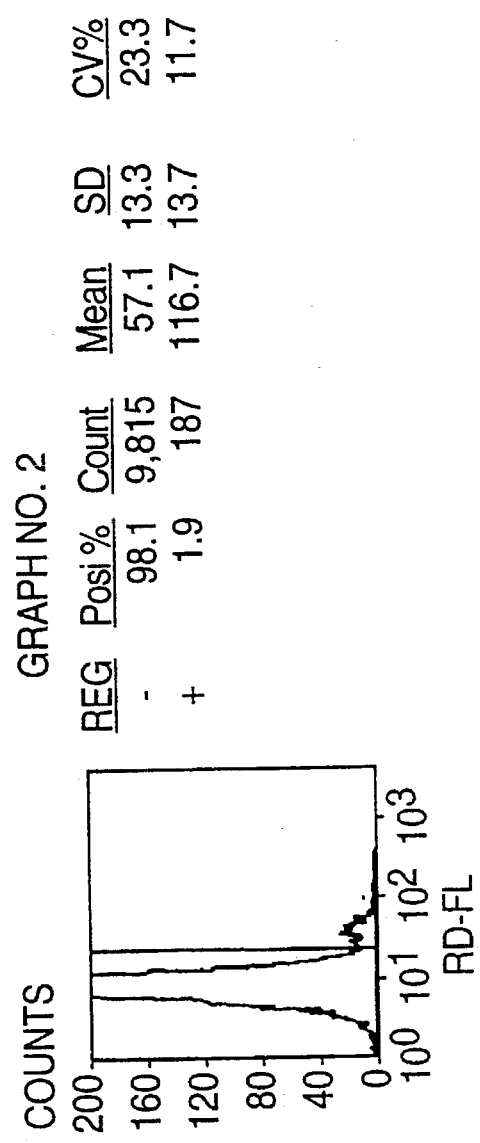
Figures 2A, 2B:
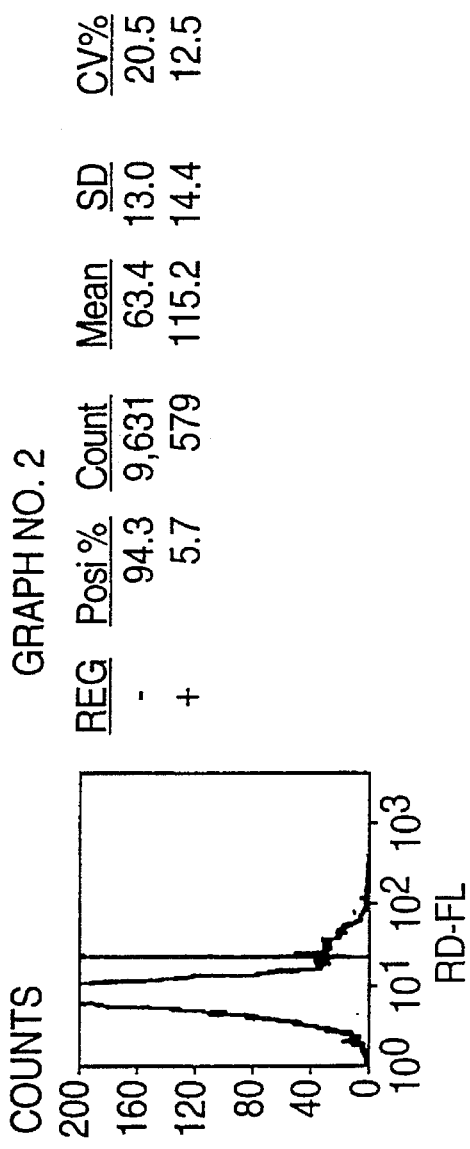
FIG. 2 shows the forward scatter versus red fluoresence cytogram and red fluorescence histogram of an abnormal blood sample stained with the fluorescent dye composition.
Figure 3A:
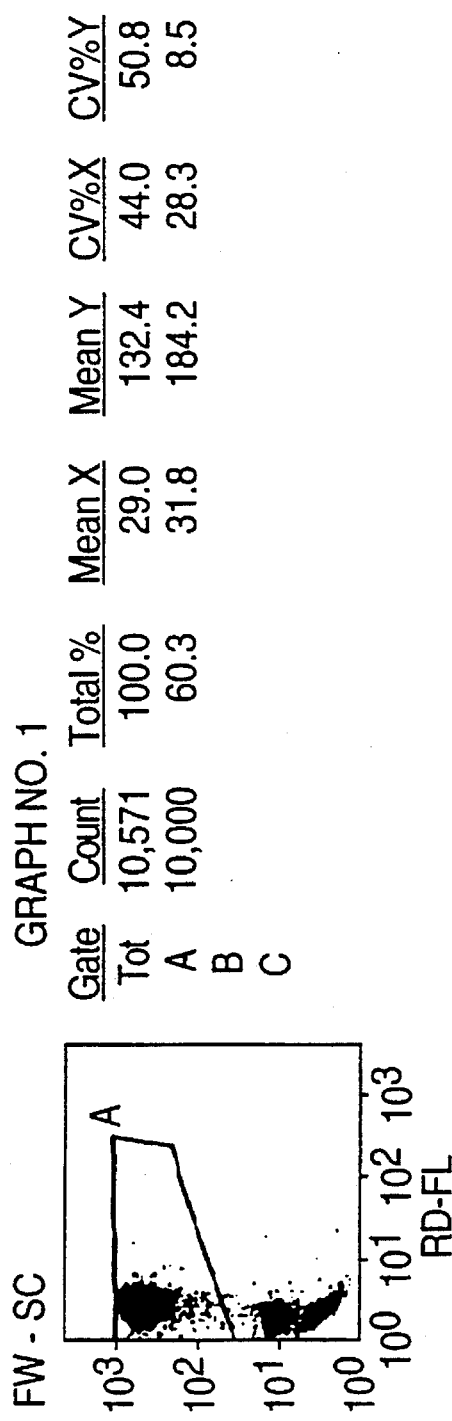
FIG. 3 shows the forward scatter versus red fluoresence cytogram and red fluorescence histogram of an unstained normal blood sample.
Figure 3B:
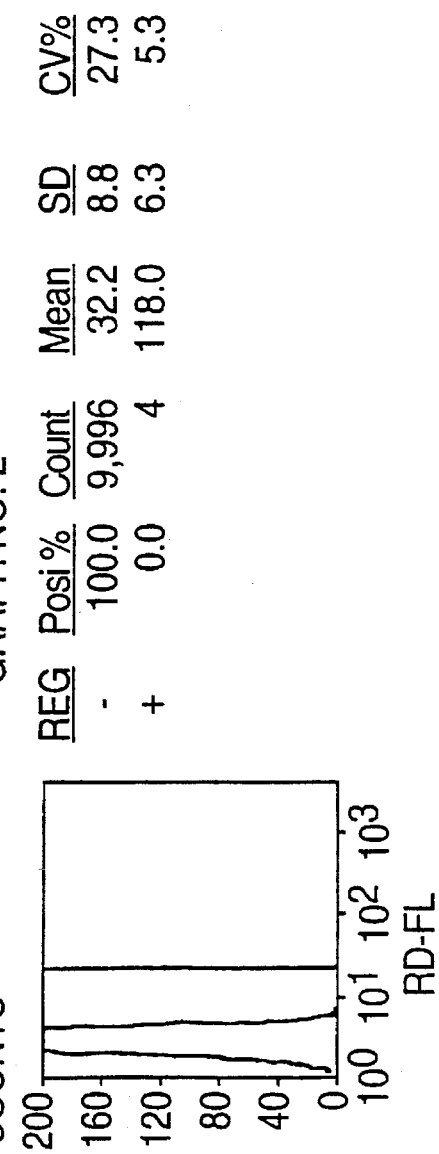

FIGS. 1 and 2 show the data generated by the above determination according to this invention for reticulocytes in the blood sample stained with the above-mentioned fluorescent dye composition and FIG. 3 shows the data similarly generated for reticulocytes in the unstained blood sample. However, FIG. 1 represents the data on stained normal blood (a sample stained 1.6% with new methylene blue), showing the forward scatter versus red fluorescence cytogram and red fluorescence histogram for the normal blood sample. FIG. 2 represents the data for stained abnormal blood (a sample stained 4.9% with new methylene blue), showing the forward scatter versus red fluorescence cytogram and red fluorescence histogram for the abnormal blood. FIG. 3 represents the data for an unstained normal blood sample, similarly showing its forward scatter versus red fluorescence cytogram and red fluorescence histogram. In the computation of measured values, the threshold given in FIG. 3 was used in FIGS. 1 and 2, with cells exceeding the threshold being regarded as reticulocytes.

Referring to FIGS. 1 through 3, FIG. 3 represents results for the unstained blood sample and provides control for the results in FIGS. 1 and 2. The decisive difference between stained and unstained samples lies in the distribution of cells in staining analysis area A (Gate A in FIG. 1). A substantially single cluster is seen in FIG. 3 but as the result of staining the dominant cluster is shifted somewhat to the right and a subsidiary cluster appears to the right of the dominant cluster. This subsidiary cluster corresponds to the cell clusters of 1.9% and 5.7% seen in the positive areas of FIGS. 1 and 2, respectively, which are clusters specifically stained with the fluorescent dye according to this invention. These results are quite similar to the results of the conventional determination using new methylene blue, suggesting the validity and usefulness of this invention.

Example 2

A 1 mM stock fluorescent dye solution (POPO-3 or PO-PRO-3/DMBO) is prepared. This stock solution is diluted 20-fold with isotonic phosphate buffer at pH 7.4 and 5 µl of whole blood is added to 1 ml of the diluted fluorescent dye composition. The mixture is incubated at room temperature for about 30 minutes and this sample is analysed with a flow cytometer using a green helium-neon laser having an excitation wavelength of 543 nm, a green super bright LED or a green laser diode as the light source.

Figure 4A:
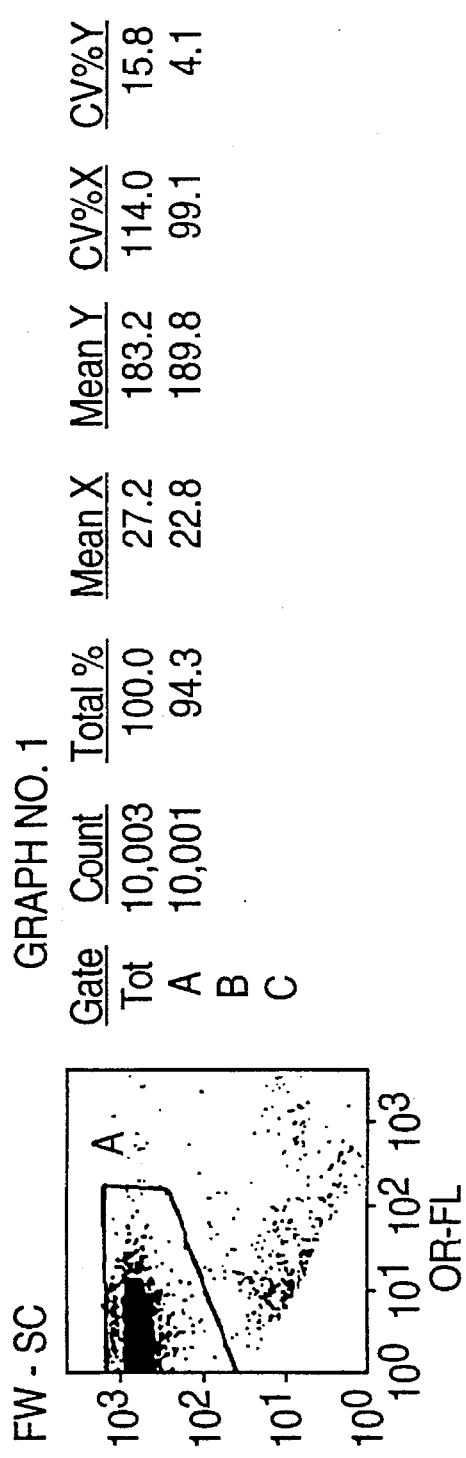
FIG. 4 shows the forward scatter versus orange fluorescence cytogram and orange fluorescence histogram of a normal blood sample stained with the fluorescent dye composition.
Figure 4B:
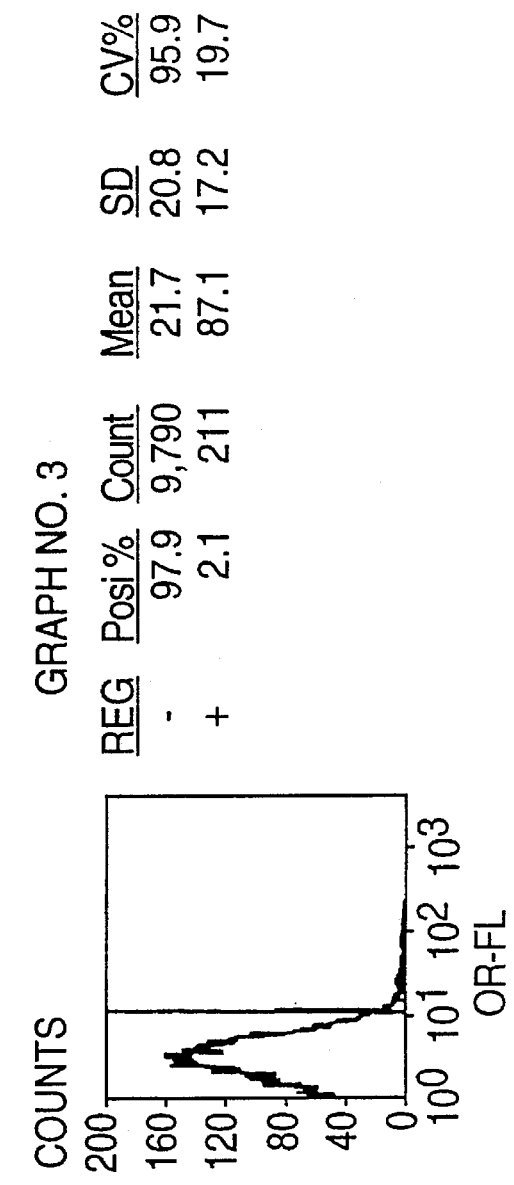
Figure 5A:
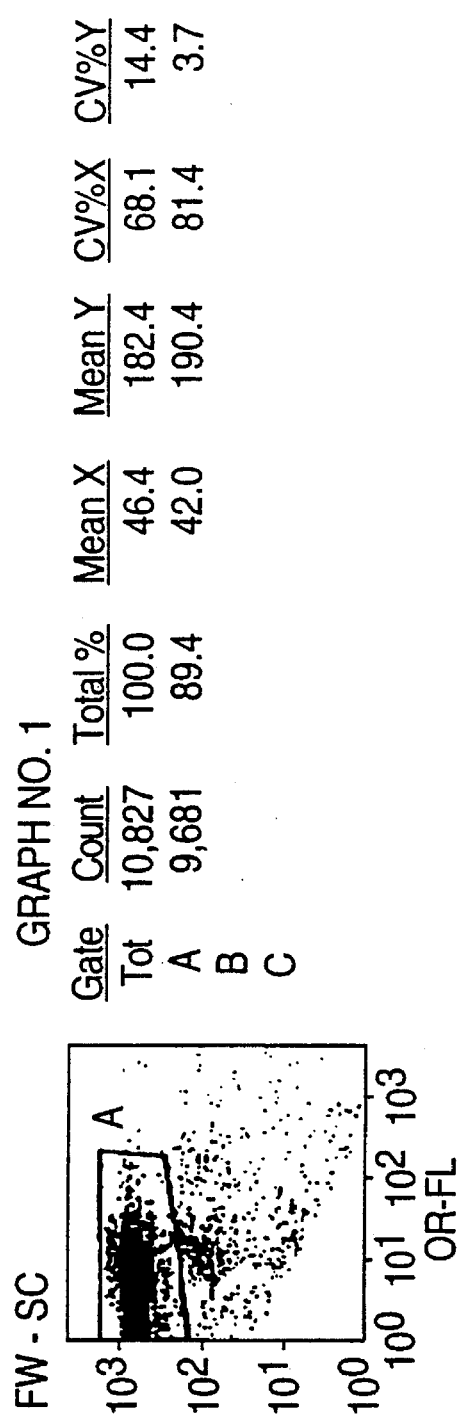
FIG. 5 shows the forward scatter versus orange fluorescence cytogram and orange fluorescence histogram of an abnormal blood sample stained with the fluorescent dye composition.
Figure 5B:
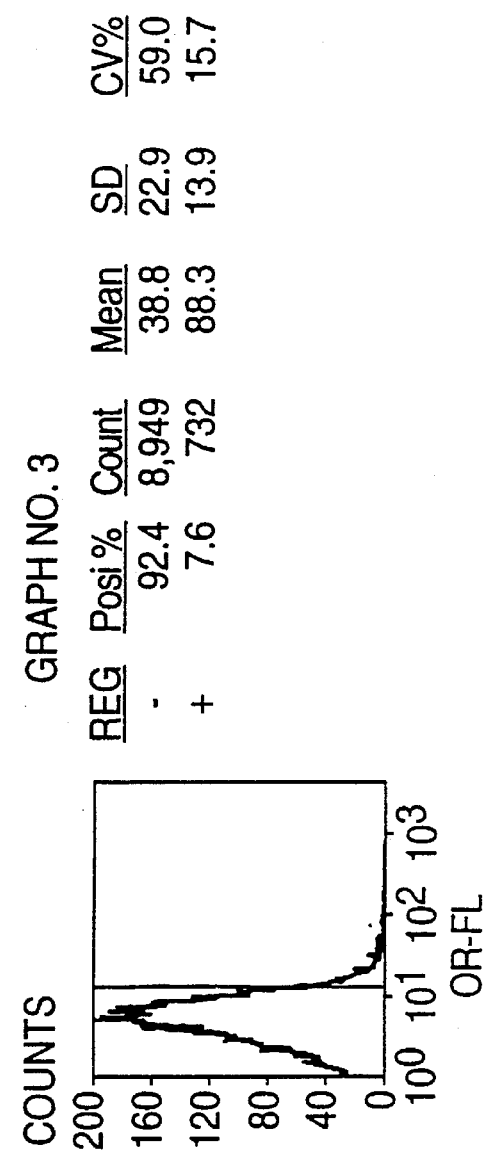
Figure 6A:
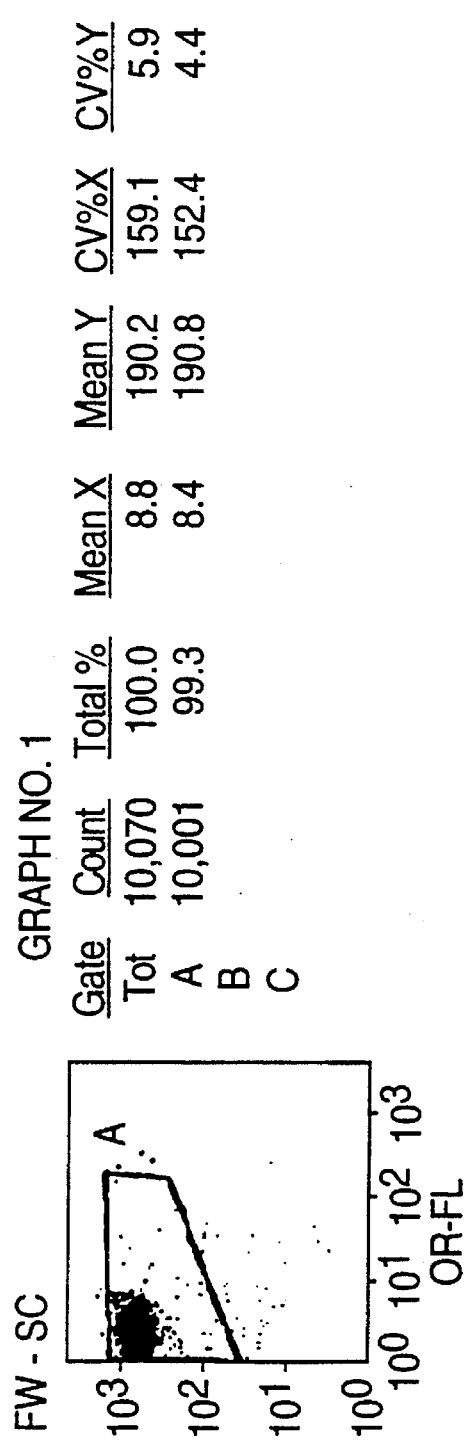
FIG. 6 shows the forward scatter versus orange fluorescence cytogram and orange fluorescence histogram of an unstained normal blood sample.
Figure 6B:
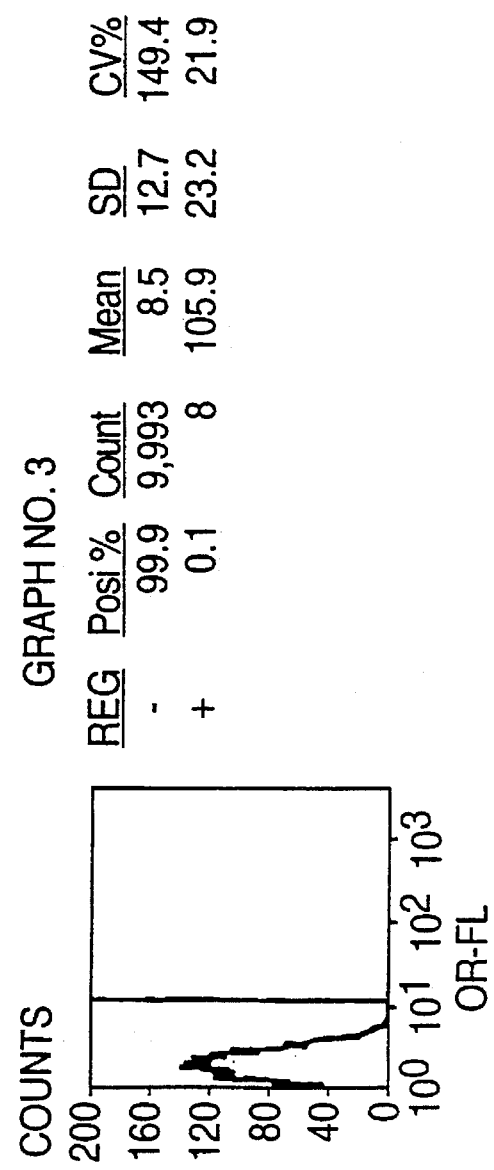

The data generated by the enumeration method of this invention are shown in FIGS. 4 through 6. However, FIG. 4 represents the data for stained normal blood (a sample stained 1.6% with new methylene blue), showing the forward scatter versus orange fluorescence cytogram and orange fluorescence histogram of the normal blood. FIG. 5 represents the data generated with stained abnormal blood (a sample stained 5.3% with new methylene blue), similarly showing the forward scatter versus orange fluorescence cytogram and orange fluorescence histogram of the abnormal blood. FIG. 6 represents the data for the unstained normal blood sample, showing its forward scatter versus orange fluorescence cytogram and orange fluorescence histogram in a similar fashion.

Example 3

A 1 mM stock fluorescent dye solution (YOYO-1 or YO-PRO-1/DMSO) is diluted 20-fold with isotonic phosphate buffer at pH 7.4 and 5 µl of whole blood is added to 1 ml of the diluted fluorescent dye composition. This system is incubated at room temperature for about 30 minutes to prepare a sample and flow cytometry is carried out using a blue argon ion laser having an excitation wavelength of 488 nm, a blue super bright LED or a blue laser diode as the light source.

Figure 7A:
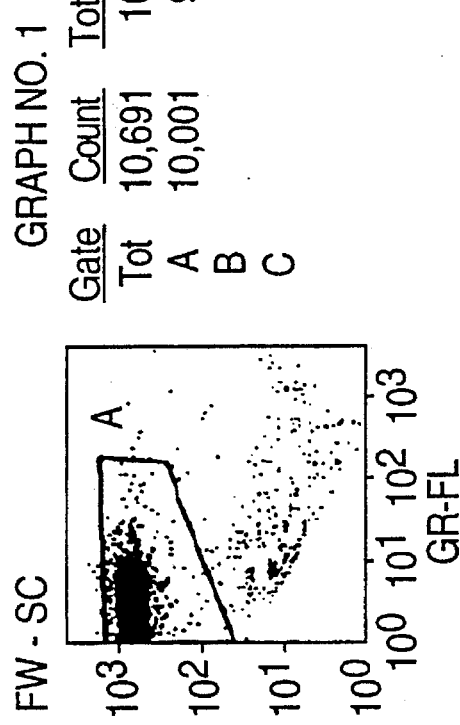
FIG. 7 shows the forward scatter versus green fluorescence cytogram and green fluorescence histogram of a normal blood sample stained with the fluorescent dye composition.
Figure 7B:
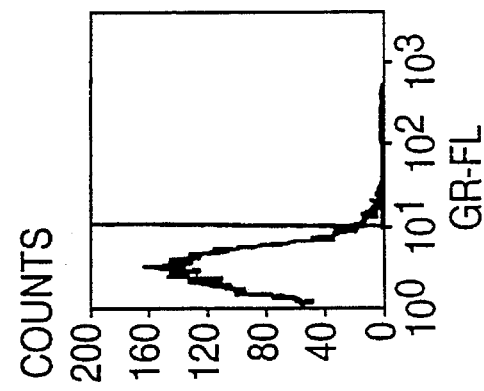
Figure 8A:
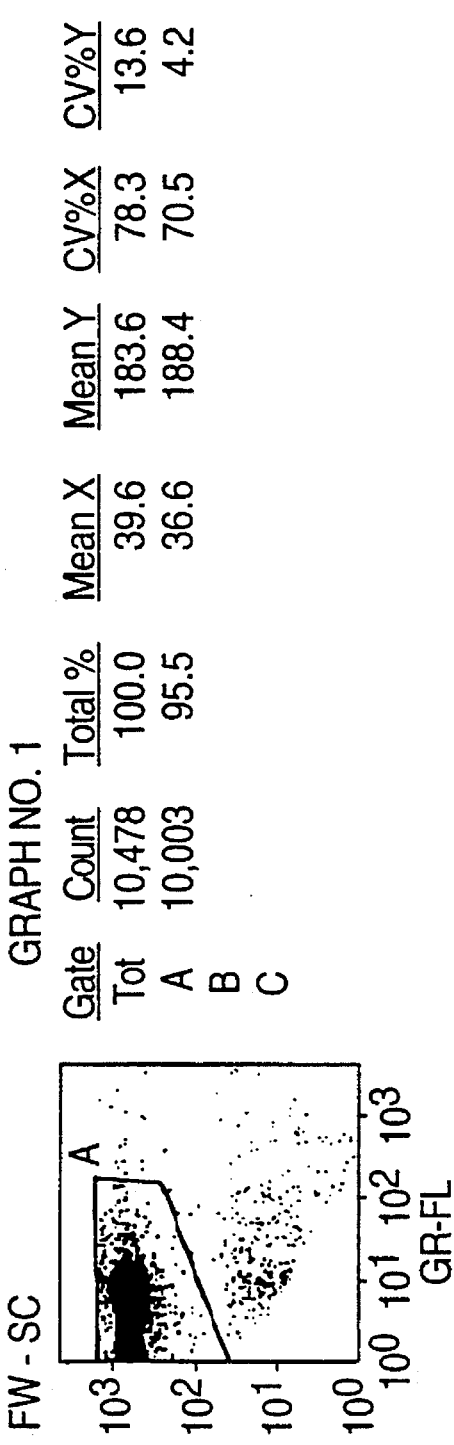
FIG. 8 shows the forward scatter versus green fluorescence cytogram and green fluorescence histogram of an abnormal blood sample stained with the fluorescent dye composition.
Figure 8B:
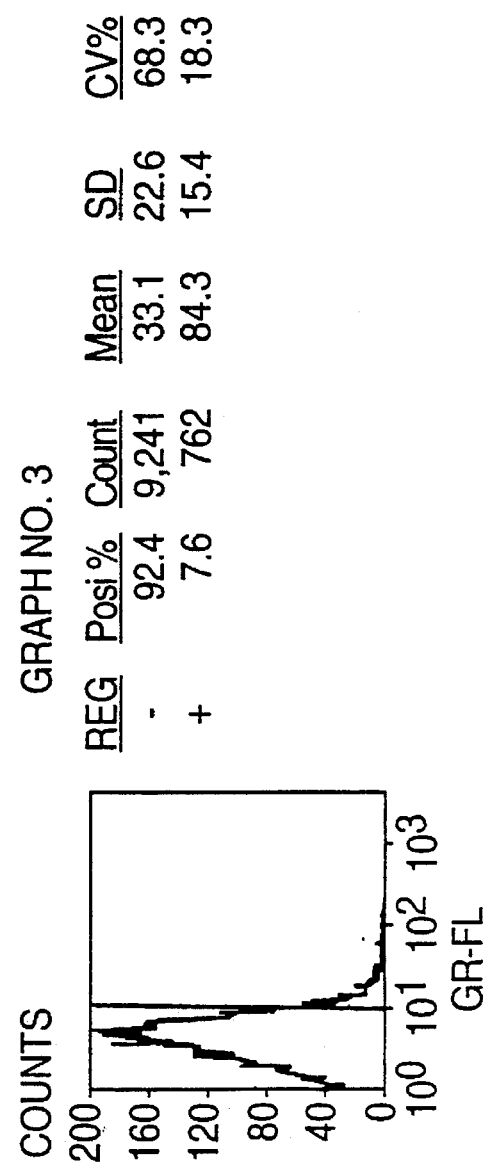
Figure 9A:
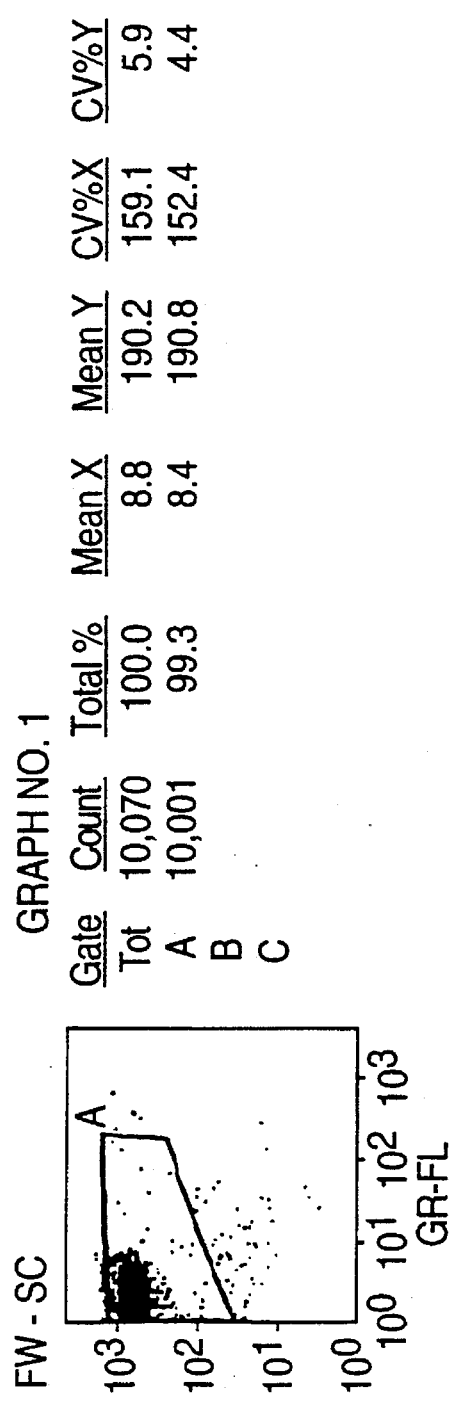
FIG. 9 shows the forward scatter versus green fluorescence cytogram and green fluorescence histogram of an unstained normal blood sample.
Figure 9B:
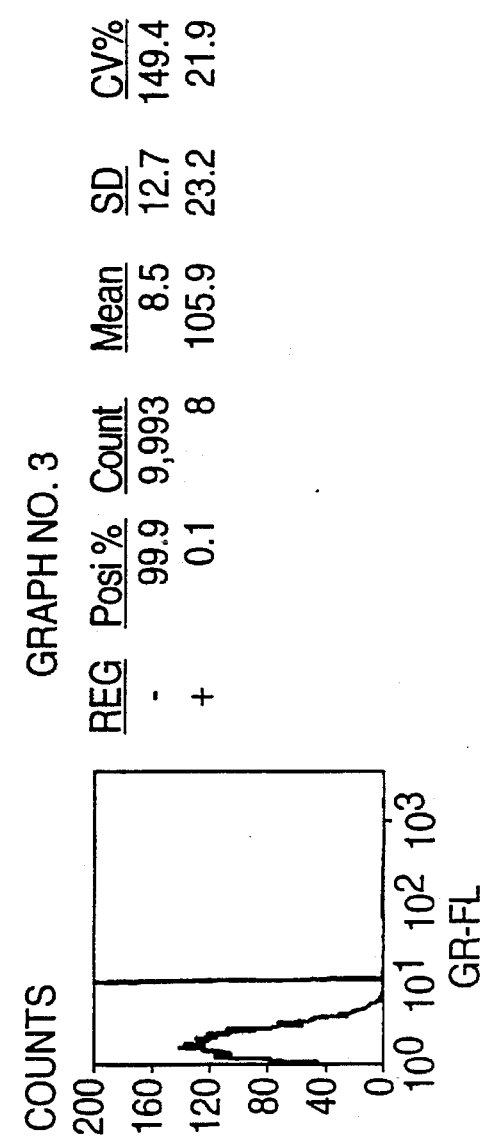

The data generated by the determination method of this invention are shown in FIGS. 7 through 9. However, FIG. 7 represents the data for stained normal blood (a sample stained 1.6% with new methylene blue), showing its forward scatter versus green fluorescence cytogram and green fluorescence histogram. FIG. 8 represents the data for stained abnormal blood (a sample stained 5.3% with new methylene blue), similarly showing the forward scatter versus green fluorescence cytogram and green fluorescence histogram of abnormal blood. FIG. 9 represents the data for unstained normal blood, similarly showing its forward scatter versus green fluorescence cytogram and green fluorescence histogram.

Example 4

A 1 mM stock fluorescent dye solution (YOYO-3 or YO-PRO-3/DMSO) is diluted 20-fold with isotonic phosphate buffer at pH 7.4 and 5 µl of whole blood is added to 1 ml of the diluted fluorescent dye composition. This system is incubated at room temperature for about 30 minutes and flow cytometry is performed using an orange helium-neon laser having an excitation wave-length of 594 nm, an orange super bright LED or an orange laser diode as the light source.

Figure 10A:
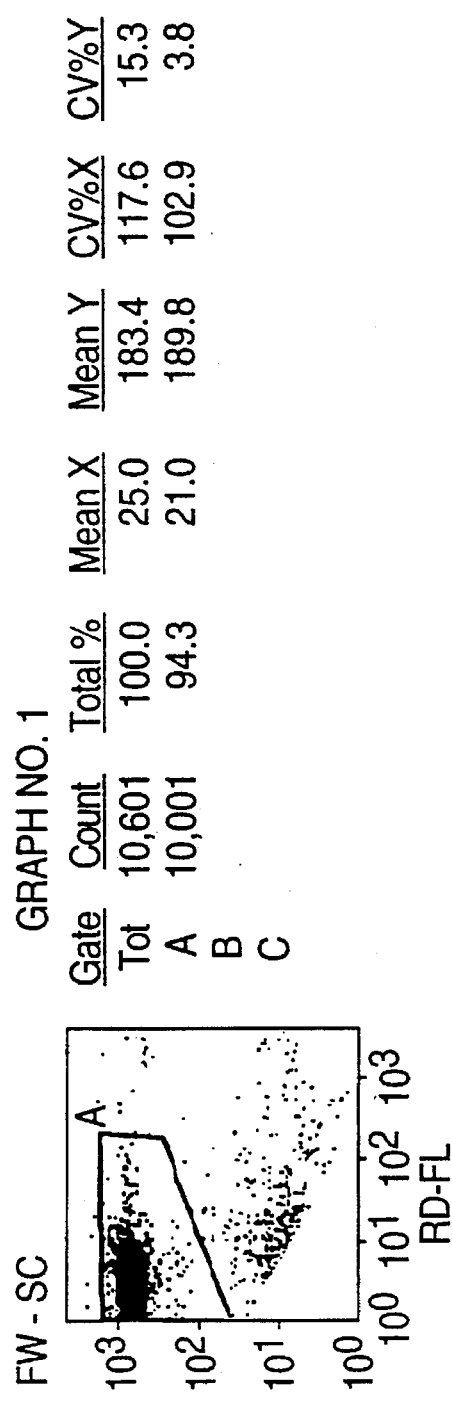
FIG. 10 shows the forward scatter versus orange fluorescence cytogram and orange fluorescence histogram of a normal blood sample stained with the fluorescent dye composition.
Figure 10B:
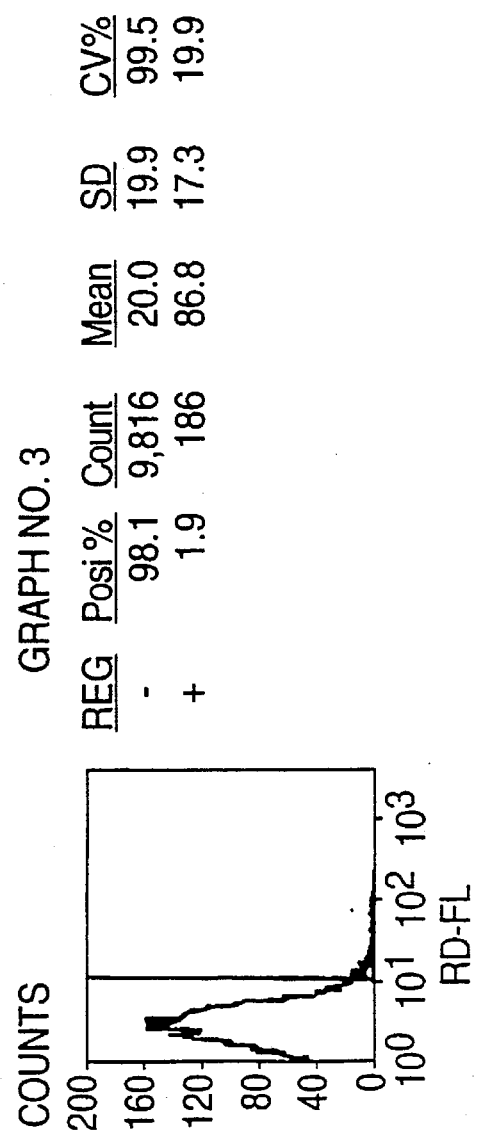
Figure 11A:
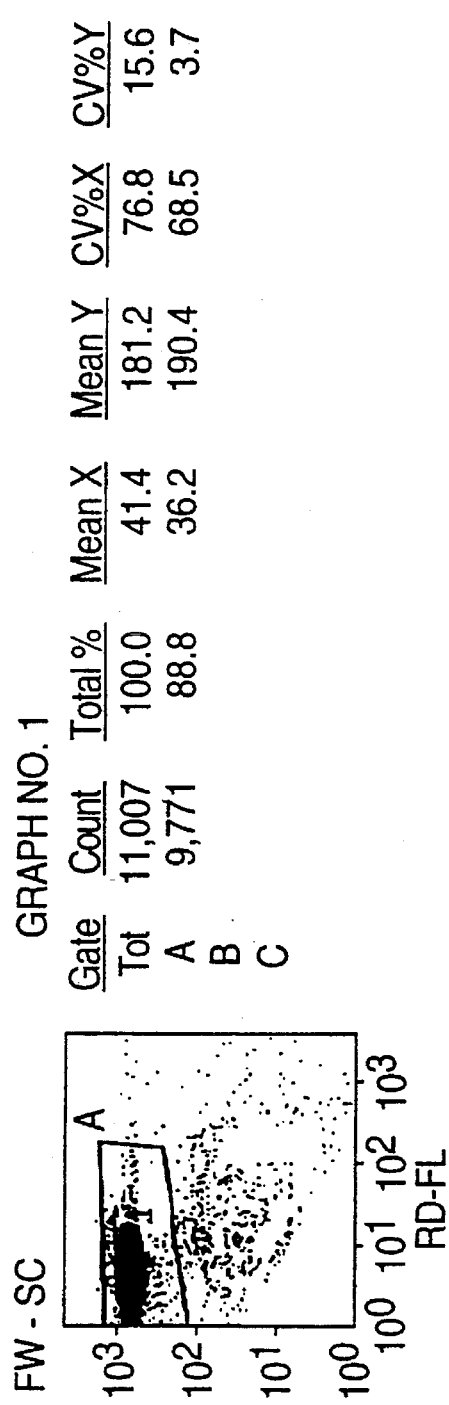
FIG. 11 shows the forward scatter versus orange fluorescence cytogram and orange fluorescence histogram of an abnormal blood sample stained with the fluorescent dye composition.
Figure 11B:
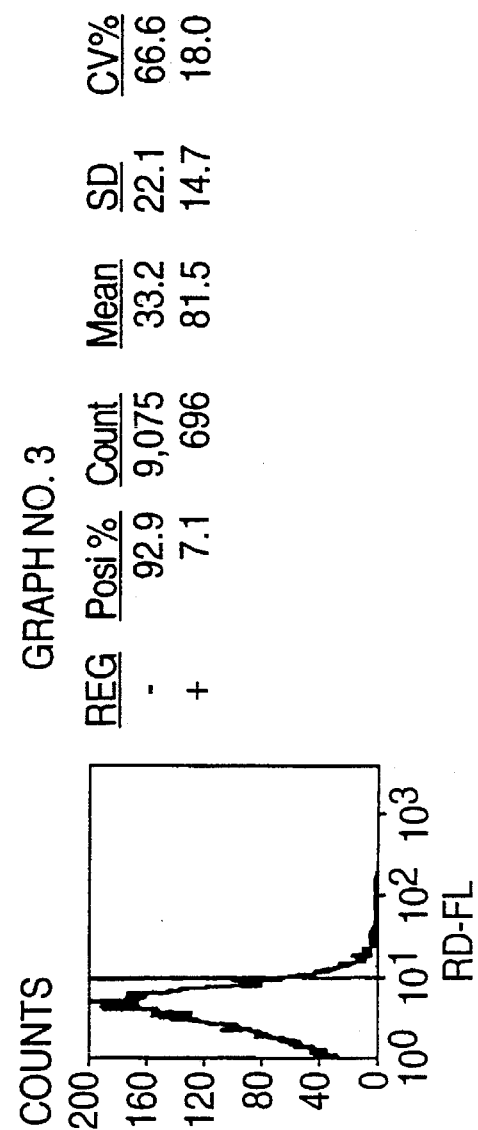
Figure 12A:
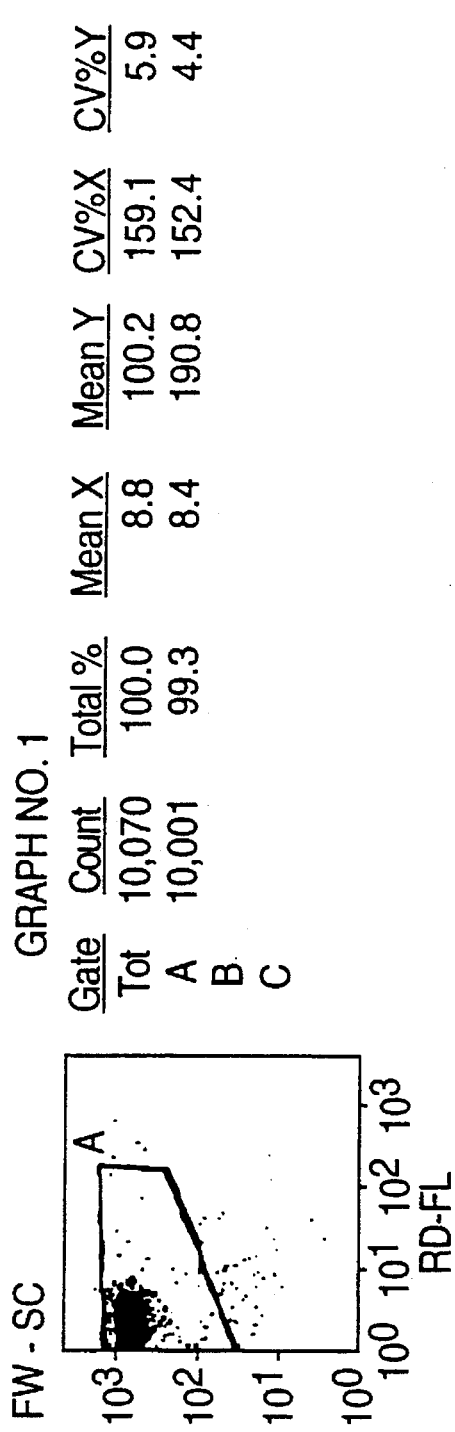
FIG. 12 shows the forward scatter versus orange fluorescence cytogram and orange fluorescence histogram of an unstained normal blood sample.
Figure 12B:
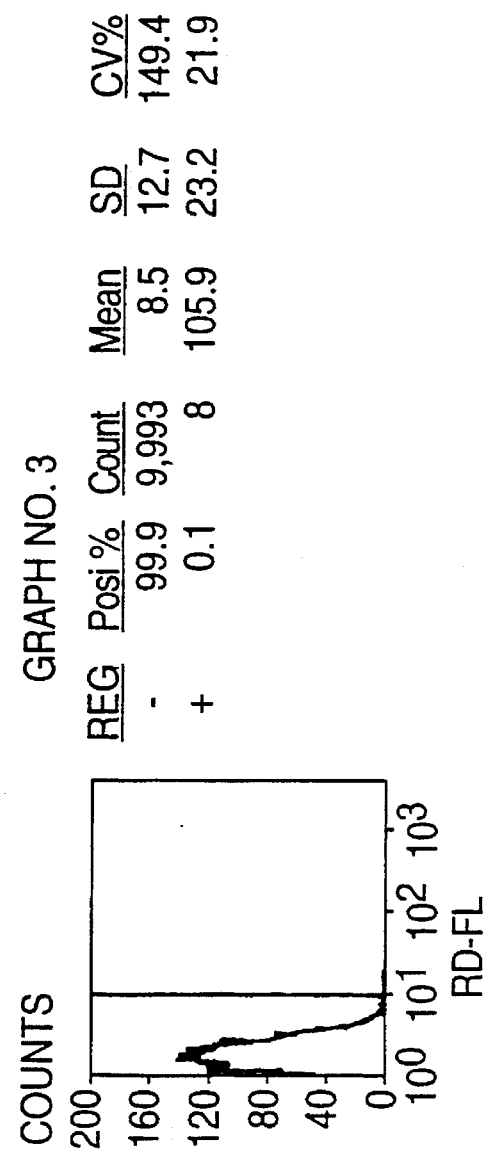

The data generated by the determination and analysis by the method of this invention are presented in FIGS. 10 through 12. However, FIG. 10 represents the data for stained normal blood (a sample stained 1.6% with new methylene blue), showing the forward scatter versus red fluorescence cytogram and red fluorescence histogram of the normal blood. FIG. 11 represents the data for stained abnormal blood (a sample stained 5.3% with new methylene blue), similarly showing the forward scatter versus red fluorescence cytogram and red fluorescence histogram of abnormal blood. FIG. 12 represents the data for the unstained normal blood sample, showing the forward scatter versus red fluorescence cytogram and red fluorescence histogram of the normal blood.

Referring to FIGS. 1 through 12 for the above Examples 1 through 4, the following abbreviations are used.

The apparatus according to this invention for quantitating reticulocytes is now described.

Figure 13:
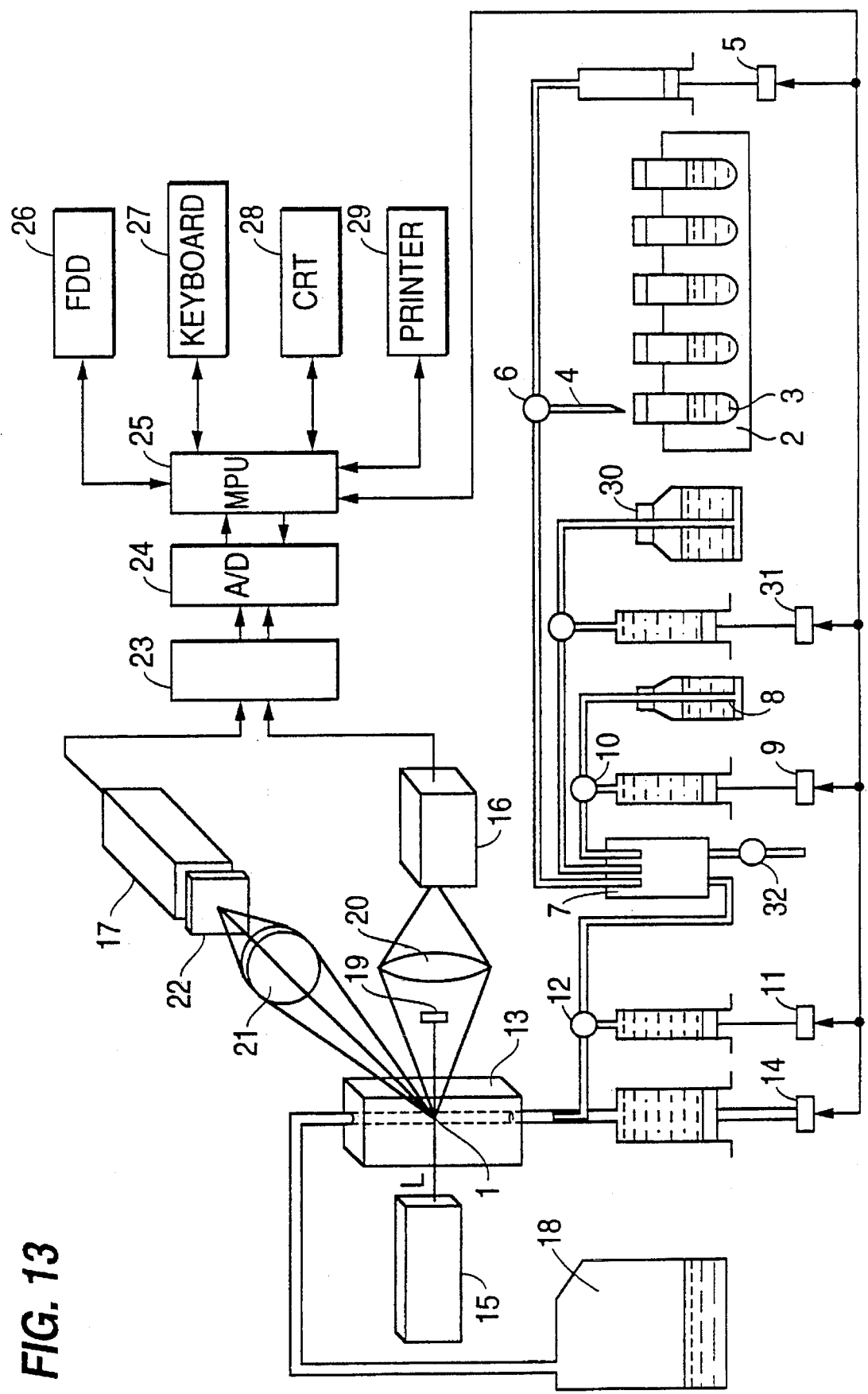
FIG. 13 shows construction of an apparatus for quantitating reticulocytes according to this invention.

Referring to FIG. 13 which shows the construction of the apparatus for quantitating reticulocytes according to this invention, a blood sample 1 in a predetermined quantity is taken from a blood sampling tube 3 set in an autosampler 2 as the cap of the tube 3 is pierced by a cap piercer 4 driven by a driving mechanism not shown and a predetermined amount of blood is transferred from the blood sampling tube 3 by a blood dispensing pump 5. Then, a 3-way valve 6 is switched, whereupon the blood is transferred to a reaction vessel 7. Indicated by the numeral 8 is a dye bottle containing said fluorescent dye composition. The dye composition is metered out by a dye composition pump 9 and, on switching of a 3-way valve 10, transferred to the reaction vessel 7. In the reaction vessel 7, the blood sample and the dye composition are incubated together for a predetermined time, after which the mixture is withdrawn by a sample pump 11 and, on switching of a 3-way valve 12, is transferred to a flow cell 13. Connected to the flow cell 13 is a sheathed liquid pump 14 and according to the principle of hydrodynamic focusing, the blood sample 1 flows linearly on the central axis of the flow cell 13.

Disposed on one side of the flow cell 13 is a light source 15, e.g. a laser diode, and the beam of light L from the light source 15 irradiates the blood sample 1 in the flow cell 13. The resulting light signals are detected by a forward scatter sensor 16 disposed in the direction of advance of beam L and a fluorescence sensor 17 disposed in the direction perpendicular to the direction of advance of beam L. After the detection, the blood sample 1 is withdrawn from the flow cell 13 and transferred to an used blood tank 18.

A beam blocker 19 for avoiding direct light and a condensor 20 are interposed between the flow cell 13 and the forward scatter sensor 16. Furthermore, a condensor 21 and an interference filter 22 are interposed between the flow cell 13 and fluorescence sensor 17.

The light signals incident on said forward scatter sensor 16 and fluorescence sensor 17 are trimmed of noise and amplified in a signal processing circuit 23, digitalized in an A/D converter 24 and fed to an MPU 25. The MPU 25 is connected to various input-output devices such as a floppy disk drive 26, a keyboard 27, a CRT 28 and a printer 29. Moreover, the MPU 25 has the function to drive and control the blood dispensing pump 5, dye composition pump 9, sample pump 11, sheathed liquid pump 14, and a cleaning solution pump 31 for feeding a cleaning solution from a cleaning solution bottle 30 to the reaction vessel 7. After the reaction vessel 7 has been cleaned with the cleaning solution, a switch valve 32 is opened to drain the vessel.

Graph No. 1
FW-SC: forward scatter intensity
RD-FL: red fluorescence intensity
OR-FL: orange fluorescence intensity
GR-FL: green fluorescence intensity
Gate: enclosed area A, which is analyzed
Count: number of cells
Total: (sometimes abbreviated as Tot. Total % is the percentage relative to the total cell population indicated in Graph No. 1.
Mean X: mean of X-axis parameter values
Mean Y: mean of Y-axis parameter values
CV%X: coefficient of variation for X-axis parameter (S.D./mean)
CV%Y: coefficient of variation for Y-axis parameter (S.D./mean)

Graph No. 2 and No. 3
Counts: The number of cells analyzed in the graph
RD-FL: red fluorescence intensity
OR-FL: orange fluorescence intensity
GR-FL: green fluorescence intensity
REG: trigger area of data analysis. In this case, there are a positive area (+) and a negative area (−).
Posi: positive %, representing the rate of positivity.
Count: number of cells present in each area
Mean: mean of X-axis parameter values for cells present in each area
SD: standard deviation of the values
CV%: coefficient of variation [(S.D./means)×100].

As described above, the method of quantitating reticulocytes according to this invention comprises exposing a blood sample stained with a fluorescent dye composition containing TOTO-3 or TO-PRO-3, POPO-3 or PO-PRO-3, YOYO-1 or YO-PRO-1, or YOYO-3 or YO-PRO-3 as the fluorescent dye to light in the red wavelength region in the case of TOTO-3 or TO-PRO-3, light in the green wavelength region in the case of POPO-3 or PO-PRO-3, light in the blue wavelength region in the case of YOYO-1 or YO-PRO-1 or light in the orange wavelength region in the case of YOYO-3 or YO-PRO-3 and measuring the output fluorescence from said blood sample to thereby quantitate reticulocytes with high sensitivity and accuracy and at low cost.

Furthermore, the flow cytometry according to this invention, employing a blood sample stained with the above fluorescent dye composition, offers the advantage of expedient reticulocyte quantitation with good sensitivity with a minimum of fluorescent background. Moreover, because the staining is performed with a composition containing the above-mentioned fluorescent dye, the intracellular RNA of reticulocytes is not precipitated and a first-order relation can be obtained between RNA content and fluorescence intensity, thus offering the advantage of providing clinically useful information.

Furthermore, the light source corresponding to the excitation wavelength of the fluorescent dye composition, viz. a red helium-neon laser, a red super bright LED or a red laser diode can be utilized for TOTO-3 or TO-PRO-3, a green helium-neon laser, a green super bright LED or a green laser diode for POPO-3 or PO-PRO-3, a blue argon ion laser, a blue super bright LED or a blue laser diode for YOYO-1 or YO-PRO-1, or an orange helium-neon laser, an orange super bright laser or an orange laser diode for YOYO-3 or YO-PRO-3, so that compared with flow cytometry using a discharge type laser as the light source, the equipment necessary for determination may be reduced in size, loss costly and simple in construction.

What is claimed is:

1. A method of characterizing reticulocytes, comprising the steps of: exposing a blood sample comprising living reticulocytes stained with a fluorescent dye composition containing

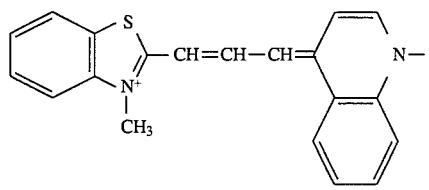

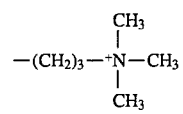

as the fluorescent dye to light in the red wavelength region, measuring the output fluorescence from said blood sample and correlating the measured fluorescence with one of the number of reticulocytes in the sample and clinical information of the reticulocytes.

2. A method of characterizing reticulocytes, comprising the steps of: exposing a blood sample comprising living reticulocytes stained with a fluorescent dye composition containing

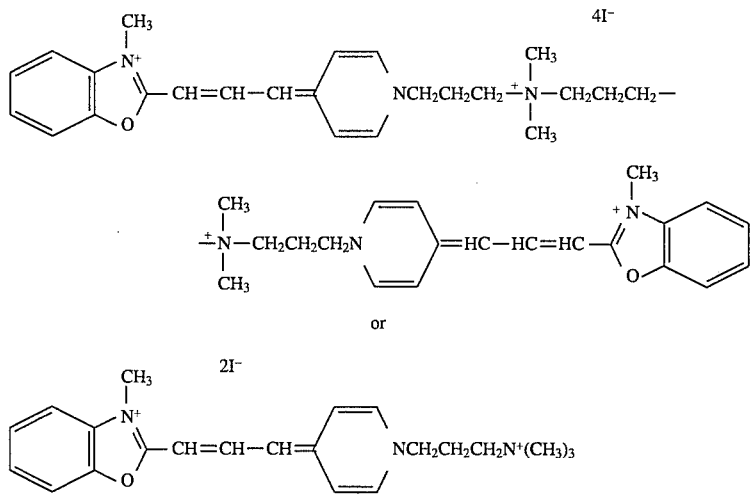

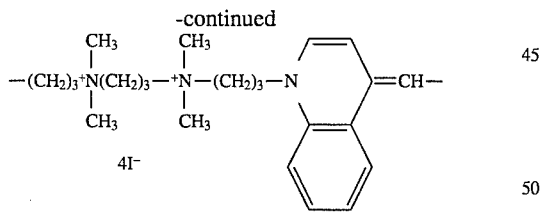

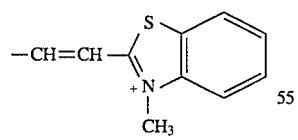

or

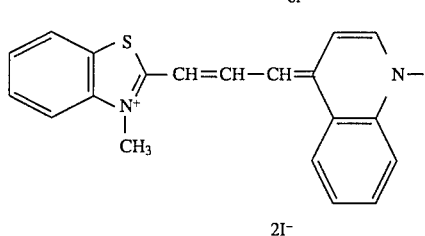

as the fluorescent dye to light in the green wavelength region, measuring the output fluorescence from said blood sample and correlating the measured fluorescence with one of the number of reticulocytes in the sample and clinical information of the reticulocytes.

3. A method of characterizing reticulocytes, comprising the steps of: exposing a blood sample comprising living reticulocytes stained with a fluorescent dye composition containing

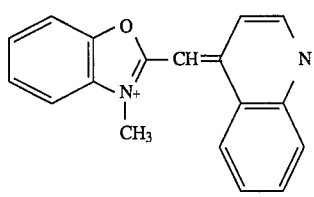 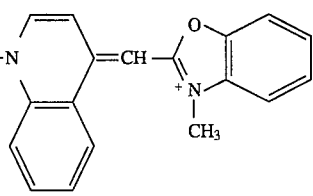

4I⁻ or

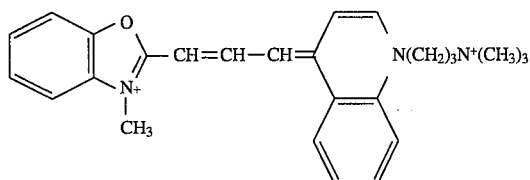

2I⁻ as the fluorescent dye to light in the blue wavelength region, measuring the output fluorescence from said blood sample and correlating the measured fluorescence with one of the number of reticulocytes in the sample and clinical information of the reticulocytes.

4. A method of characterizing reticulocytes, comprising the steps of: exposing a blood sample comprising living reticulocytes stained with a fluorescent dye composition containing

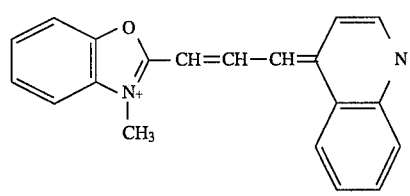 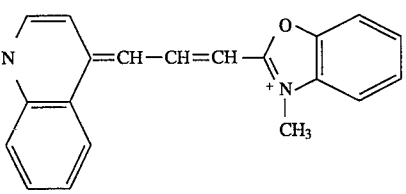

4I⁻ or

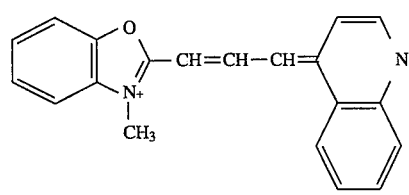

2I⁻ as the fluorescent dye to light in the orange wavelength region, measuring the output fluorescence from said blood sample and correlating the measured fluorescence with one of the number of reticulocytes in the sample and clinical information of the reticulocytes.

5. The method of quantitating reticulocytes according to claim 1 wherein reticulocytes in the blood sample stained with said fluorescent dye composition are quantitated by flow cytometry using light from a helium-neon laser.

6. The method of quantitating reticulocytes according to claim 1 wherein reticulocytes in the blood sample stained with said fluorescent dye composition are quantitated by flow cytometry using light from a super bright LED.

7. The method of quantitating reticulocytes according to claim 1 wherein reticulocytes in the blood sample stained with said fluorescent dye composition are quantitated by flow cytometry using light from a laser diode.

8. The method of quantitating reticulocytes according to claim 2 wherein reticulocytes in the blood sample stained with said fluorescent dye composition are quantitated by flow cytometry using light from a helium-neon laser.

9. The method of quantitating reticulocytes according to claim 2 wherein reticulocytes in the blood sample stained with said fluorescent dye composition are quantitated by flow cytometry using light from a super bright LED.

10. The method of quantitating reticulocytes according to claim 2 wherein reticulocytes in the blood sample stained with said fluorescent dye composition are quantitated by flow cytometry using light from a laser diode.

11. The method of quantitating reticulocytes according to claim 3 wherein reticulocytes in the blood sample stained with said fluorescent dye composition are quantitated by flow cytometry using light from a helium-neon laser.

12. The method of quantitating reticulocytes according to claim 3 wherein reticulocytes in the blood sample stained with said fluorescent dye composition are quantitated by flow cytometry using light from a super bright LED.

13. The method of quantitating reticulocytes according to claim 3 wherein reticulocytes in the blood sample stained with said fluorescent dye composition are quantitated by flow cytometry using light from a laser diode.

14. The method of quantitating reticulocytes according to claim 4 wherein reticulocytes in the blood sample stained with said fluorescent dye composition are quantitated by flow cytometry using light from a helium-neon laser.

15. The method of quantitating reticulocytes according to claim 4 wherein reticulocytes in the blood sample stained with said fluorescent dye composition are quantitated by flow cytometry using light from a super bright LED.

16. The method of quantitating reticulocytes according to claim 4 wherein reticulocytes in the blood sample stained with said fluorescent dye composition are quantitated by flow cytometry using light from a laser diode.

* * * * *